United States Patent [19]
Steinberg et al.

[11] Patent Number: 4,563,197
[45] Date of Patent: Jan. 7, 1986

[54] PROCESS FOR THE PRODUCTION OF ETHYLENE AND OTHER HYDROCARBONS FROM COAL

[75] Inventors: Meyer Steinberg, Huntington Station; Peter Fallon, East Moriches, both of N.Y.

[73] Assignee: The United States of America as represented by the Department of Energy, Washington, D.C.

[21] Appl. No.: 580,500

[22] Filed: Feb. 15, 1984

Related U.S. Application Data

[63] Continuation-in-part of Ser. No. 349,225, Feb. 16, 1982, abandoned.

[51] Int. Cl.$^4$ .............................. C10J 3/46; C07C 1/00
[52] U.S. Cl. ........................................ 48/210; 585/638
[58] Field of Search ................... 48/210; 585/638, 734; 208/8 R

[56] References Cited

U.S. PATENT DOCUMENTS

| | | | |
|---|---|---|---|
| 2,709,675 | 5/1955 | Phinney | 201/23 |
| 3,375,175 | 3/1968 | Eddinger et al. | 201/31 |
| 3,574,065 | 4/1971 | Eddinger et al. | 201/12 |
| 3,698,882 | 10/1972 | Garrett et al. | 48/210 |
| 3,736,233 | 5/1973 | Sass et al. | 201/31 |
| 3,846,096 | 11/1974 | Mallan et al. | 48/210 |
| 3,855,070 | 12/1974 | Squires | 201/23 |
| 4,213,826 | 7/1980 | Eddinger et al. | 201/31 |
| 4,229,185 | 10/1980 | Sass | 48/197 R |

*Primary Examiner*—Peter Kratz
*Attorney, Agent, or Firm*—Margaret C. Bogosian; Robert J. Fisher; Judson R. Hightower

[57] ABSTRACT

A process for the production of economically significant amounts of ethylene and other hydrocarbon compounds, such as benzene, from coal is disclosed wherein coal is reacted with methane at a temperature in the approximate range of 500° C. to 1100° C. at a partial pressure less than about 200 psig for a period of less than 10 seconds. Ethylene and other hydrocarbon compounds may be separated from the product stream so produced, and the methane recycled for further production of ethylene. In another embodiment, other compounds produced, such as by-product tars, may be burned to heat the recycled methane.

6 Claims, 1 Drawing Figure

PROCESS FOR THE PRODUCTION OF ETHYLENE AND OTHER HYDROCARBONS FROM COAL

The United States Government has rights in this invention pursuant to Contract No.DE-AC02-76-CH00016, between the U.S. Department of Energy and Associated Universities, Inc.

RELATED APPLICATIONS

The instant application is a continuation-in-part application of co-pending U.S. patent application Ser. No. 349,225 filed Feb. 16, 1982, now abandoned.

BACKGROUND OF THE INVENTION

The subject invention relates to the production of chemical feedstocks from coal, and more particularly to the production of ethylene from coal.

With the advent of the "energy crisis" and the concomitant realization of the generally limited nature of oil and natural gas supplies, numerous efforts were begun to develop methods whereby the abundant United States deposits of coal could be used in the production of gaseous and liquid fuels. Typical of the methods developed is the method taught by Garret, et al. in U.S. Pat. No. 3,698,882, wherein particulate coal is entrained in a non-reactive gaseous stream, pyrolyzed at a temperature of about 600° F. to 1500° F., at a pressure less than 10 psi, for a period of from 0.1 to 3 seconds. The pyrolysis gases are then hydrogenated to form a pipeline gas consisting essentially of methane, hydrogen, and carbon monoxide. The non-reactive gas used in the Garrett, et al. method is preferably hydrogen, but may be nitrogen, argon, methane, carbon monoxide, mixtures thereof, or other non-reactive gases.

Similarly, numerous other patents, such as U.S. Pat. Nos. 3,375,175, 3,574,065, and 4,213,826 to Eddinger, U.S. Pat. No. 4,229,185 to Sass, U.S. Pat. No. 2,709,675 to Phinney, and U.S. Pat. No. 3,855,070 to Squires, teach various methods for the production of liquid and gaseous fuels from coal. Despite the large research effort in the field of producing gaseous and liquid fuels from coal, little attention has been given to the production of chemical feedstocks, most importantly ethylene and benzene, using coal as the raw material. According to the recent report in *Chemical and Engineering News* (volume 61, number 4, page 13, 1983), approximately 31 billion pounds of ethylene were produced in the United States in the previous year. Ethylene is an important raw material in the plastic and polymer industries and it is anticipated that the demand for ethylene will continue to increase in the future. At present, ethylene is produced mainly through thermal and catalytic hydrocracking of ethane and other hydrocarbons.

In some of the coal pyrolysis research, researchers have reported very small yields of ethylene as an undesired side product in the production of fuels. The literature shows less than 1% ethylene formation by the pyrolysis of coal at pressures ranging from vacuum to 1000 psi with short residence times. Traditionally, the pyrolysis of coal has been carried out in inert gas atmospheres such as helium or nitrogen or in reactive gas atmospheres such as hydrogen, carbon monoxide, carbon dioxide or $H_2O$. A paper by I. W. Smith of CSIRO Australia (Smith, "New Approaches to Coal Pyrolysis", Proceedings of the EPRI Conference on Coal Pyrolysis, Feb. 25-26, 1981) shows 4% ethylene yield with 1% ethane and 1% propane from the pyrolysis of Pittsburg No. 8 coal at 800° C. and 1 atmosphere pressure for a period of approximately 0.5 seconds.

At present, no coal conversion process is known which produces economically significant amounts of the chemical feedstocks ethylene and benzene. Applicants have found that the flash methanolysis of coal, that is the pyrolysis of coal under pressure in an atmosphere of methane, when conducted at appropriate temperatures and gas pressures, using appropriate solids residence tim and gas/solids ratios, results in economically significant yields of ethylene.

Thus, it is an object of the subject invention to provide a method for the production of substantial amounts of ethylene from coal.

It is another object of the subject invention to provide such a method which also produces substantial quantities of benzene and light oils.

It is still another object of the subject invention to provide a method for the production of ethylene from coal where substantially the only required raw material is coal.

BRIEF SUMMARY OF THE INVENTION

The above noted objects are achieved by the process of the subject invention, which comprises the steps of first reacting particulate coal with methane at a temperature in the approximate range of 500° C. to 1100° C. and at a partial pressure of methane of less than 200 psig for a period of less than 10 seconds. More preferably, the method of the subject invention is carried out at a temperature of approximately 850° C. to 1000° C. and a pressure of 50 psig for a period of approximately 1.5 seconds.

Surprisingly, it has been found that in the practice of the subject invention not only are commercially significant quantities of ethylene produced, namely yields in excess of 10% (percent carbon converted to product), along with economically significant quantities of benzene and light oils, namely toluene and xylene, but also that there is little, if any, net consumption of methane in the reaction and possibly even a small net production. Since it is apparent that the carbonaceous solids or "char" remaining after the reaction is carried out may be burned to provide the necessary energy to carry out the process of the subject invention, it is apparent that the subject invention advantageously provides a method for the conversion coal to economically significant quantitites of ethylene, benzene and light oils while requiring only coal and, possibly, small amounts of make-up methane.

Other objects and advantages of the subject invention will be apparent to those skilled in the art from a consideration of the attached drawings, the detailed description of the invention, and the experimental examples set forth below.

DETAILED DESCRIPTION OF A PREFERRED EMBODIMENT OF THE INVENTION

Figure 1:
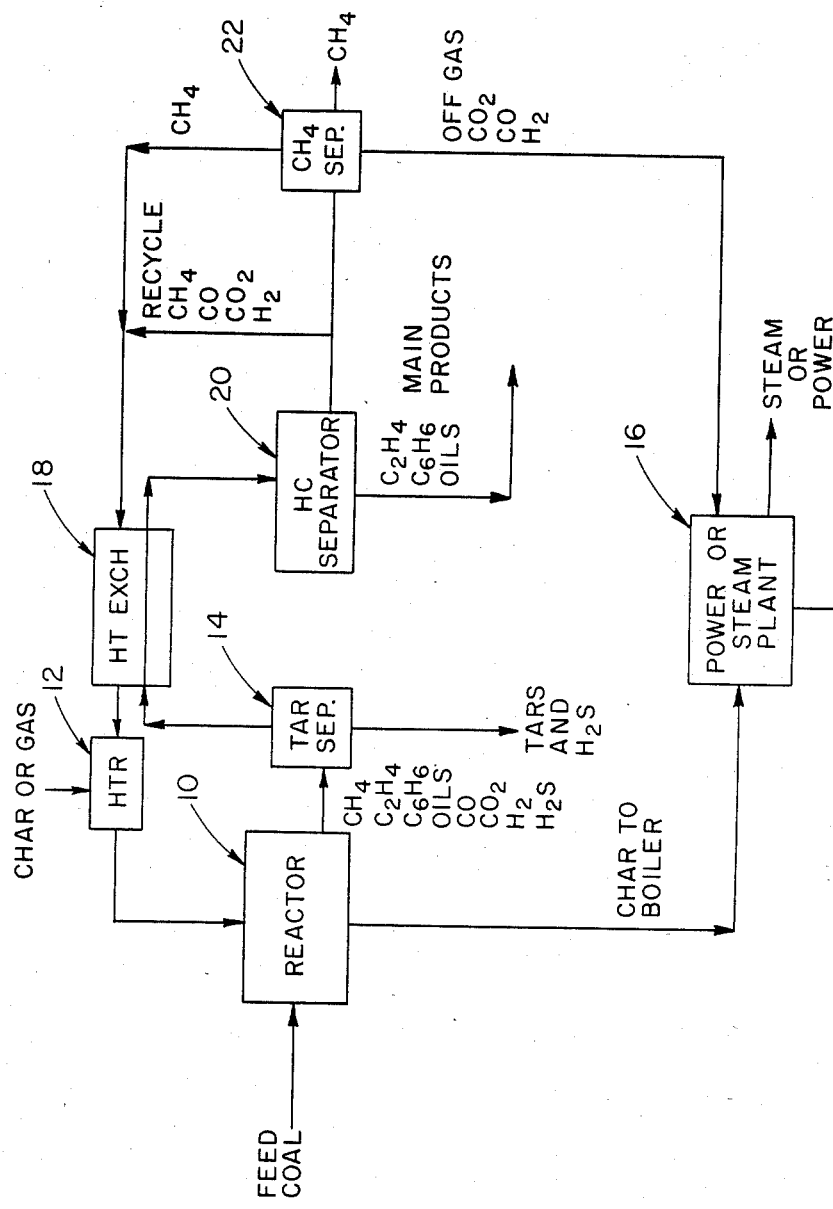
FIG. 1 is a block diagram of a chemical process in accordance with the method of the subject invention.

Turning to FIG. 1, there is shown a process in accordance with the subject invention. Coal particulates, preferably in a size range of 50 to 500 microns, are introduced to reactor 10. Methane gas heated in conventional heater 12 to a temperature of approximately 850° C. is fed into reactor 10 and reacted with the coal particulates at a pressure of approximately 50 psig for a period of approximately 2 seconds. Reactor 10 may be any conventional type of reactor vessel capable of providing the necessary reaction conditions, but is preferably a parallel flow tubular reactor.

After the reaction, a product stream comprising: methane; ethylene with possible admixtures of propylene and propane; ethane; benzene with possible admixture of toluene and xylene; light oils; carbon monoxide; carbon dioxide; hydrogen; hydrogen sulfide; and tars, is drawn off to a conventional tar separator 14, where the tars and hydrogen sulfide are removed from the product stream. The tars may then be burned to generate steam or electricity or they may be hydrocracked to produce further oils. The char is also removed from reactor 10 and burned in power or steam plant 16. The power or steam may be sold to a utility, or may be used internally in an integrated chemical plant. A small portion, approximately 10%, may be burned in heater 12 to heat the methane flow.

After removal of the tars and hydrogen sulfide the product stream passes through a heat exchanger 18 where the heat is transferred from the product stream to the methane in order to preheat the methane flow before it enters heater 12. The cooled product stream then flows through a conventional hydrocarbon separator 20 where the ethylene, benzene and light oils are separated out as the main products. (At this point any admixed propylene and propane may easily be cracked to produce additional ethylene).

After separation of the main products the gas stream consists essentially of methane with some residual carbon monoxide, carbon dioxide and hydrogen. A portion of this gas stream flows through a conventional methane separator 22 where the residual gases are removed. The methane from separator 22 is then combined with the gas flow from hydrocarbon separator 20 and the combined flow is recycled through heat exchanger 18 to be returned to heater 12 and reactor 10. The portion of the gas flow from hydrocarbon separator 20 which should flow through methane separator 22 is dependent on the rate of build-up of residual gases; which in turn will depend upon details of the process design and may best be determined by routine experimentation, and should be chosen to keep the level of residual gases in the recycled methane flow below about 20%.

Table 2 shows the methane and total gas flow data, at steady reactor operating conditions, for several runs. The difference between the methane flows indicates a negligible net consumption or production of methane which has been estimated to be approximately ±3%.

The residual gases separated from the recycled methane flow may also be burned as fuel or may be used as synthesis gas in further chemical processes.

Table 1 shows a proximate and ultimate analysis (Wt%) of the New Mexico sub-bituminous coal used in the experiments.

Based on stoichiometric considerations, improved yields of ethylene may be obtained by using a coal having a lower oxygen content.

EXPERIMENTAL EXAMPLES

A number of experiments were conducted to determine optimum reaction conditions for the inventive process. Coal particulates were entrained in a process gas stream in a one-inch tubular reactor under the conditions shown in Tables 3-8. This reactor is a highly instrumented down-flow entrained tubular reactor made of Inconel TM 617 alloy; the reactor is heated electrically by four clam-shell type heaters and designed for a maximum pressure of 4000 psi. Further details of the construction of the reactor may be found in Brookhaven National Laboratory Report No. 50698 (January 1977), available from National Technical Information Service, 5285 Port Royal Road, Springfield, Va. 2216, which is hereby incorporated by reference.

Coal particulates of 50-500 microns in diameter, mixed with 10% by weight of an agent that enhances particle flow such as Cab-O-Sil TM, are fed by gravity at the rate of approximately one pound/hour into the top of the reactor. Methane is preheated to 600° C. before feeding into the tubular reactor held at isothermal conditions along the length of the reactor at the temperature of interest.

Table 3 shows the effect of the methane gas pressure on the yields of ethylene and benzene.

Table 4 shows the effect of the reactor temperature on the yields of ethylene and benzene.

The following points should be noted:

1. When methane alone is run through the reactor at 900° C. and 200 psi (run 451A Table 3) there was no formation of higher gaseous or liquid hydrocarbons. It was also noted that a very small amount of carbon coated the surfaces of the 1" tubular reactor and none was found in the char trap. It appears there was no gross heterogeneous decomposition of methane on the hot surfaces of the reactor. 2. Upon running methane with coal at 900° C. starting at 2000 psi and following the ethylene with decreasing pressure, there is no ethylene formation until the system pressure is reduced to below 1000 psi. As seen in Table 3, at 500 psi the ethylene yield is 4.3% and it continues to rise to 10.0% at 50 psi.

3. As seen in Table 3, the benzene (BTX) yield fluctuates between 6.5% and 2.9% between pressures of 500 psi and 50 psi.

Tables 5-8 show results of the flash pyrolysis of coal using different gaseous atmospheres. Table 5 shows the process of the present invention as the flash pyrolysis is conducted in methane. Tables 6, 7, and 8 show the flash pyrolysis being conducted using the gases that have been used in prior art coal pyrolysis processes to prepare liquid and gaseous fuels.

As seen in Table 5, as high as 12.7% carbon was converted to ethylene at 1000° C. and approximately 9% was converted to BTX. In contrast, as seen in Table 8, pyrolysis in inert helium atmosphere produced only 2.3% ethylene and 1.8% BTX under the same conditions. Thus, at 1000° C., a 5-6 times greater yield of ethylene is produced during the flash methanolysis of the present invention when compared to helium pyrolysis. When the coal was pyrolyzed under the same reaction conditions using carbon monoxide as the atmosphere, 2.6% ethylene was produced and 1.8% BTX, as seen in Table 7. Table 6 shows that when the flash pyrolysis is conducted in nitrogen atmosphere at 1000° C. and 50 psi, the yield of ethylene is 3.2% and BTX 2.0%.

It is apparent from these comparative runs that the success of the present invention in obtaining commercially significant yields of ethylene and benzene is due to the fact that under the reaction conditions employed, the methane reacts with the coal to favor the formation of ethylene and benzene.

TABLE 1

| | |
|---|---|
| Moisture* | 7.8 |
| Proximate Analysis | |
| Dry Ash | 22.8 |
| Dry V.M | 34.9 |
| Dry FC | 42.4 |
| Ultimate Analysis | |
| Carbon | 55.9 |
| Hydrogen | 4.3 |
| Nitrogen | 1.1 |
| Sulfur | 1.0 |
| Oxygen** | 14.9 |

*As received
**By difference

TABLE 2

Mass Flowmeter Data

| Run No. | Pressure (psi) | Temp. (°C.) | Feed Methane In (SCF/min)[1] | Total Gases Out (SCF/min) | % Methane in Exit Gases | Methane Out (SCF/min) | % Difference in Methane Flow |
|---|---|---|---|---|---|---|---|
| 643[2] | 20 | 1000 | 0.88 | 1.06 | 82 | 0.87 | −1.1 |
| 644[2] | 50 | 1000 | 0.93 | 1.06 | 88 | 0.93 | 0 |
| 650[3] | 50 | 900 | 1.0 | 1.10 | 88 | 0.97 | 3.0 |

[1]SCF = Standard Cubic Feet at 15° C. and 1 atm.
[2]New Mexico Sub-bituminous Coal
[3]Montana Rosebud Sub-bituminous Coal

TABLE 3

Flash Methanolysis of New Mexico Sub-bituminous Coal
Effect of Gas Pressure

| | Run No. | | | | |
|---|---|---|---|---|---|
| | 451A | 683 | 454 | 451 | 424 |
| Reactor Temp. (°C.) | 900 | 900 | 900 | 900 | 900 |
| Reactor Pressure (psi) | 200 | 50 | 100 | 200 | 500 |
| Coal Feed Rate (lb/hr.) | 0 | 0.99 | 1.22 | 0.85 | 1.05 |
| Methane Feed Rate (lb/hr.) | 4.0 | 4.05 | 3.5 | 4.0 | 5.6 |
| Coal Particle Residence Time (sec.) | — | 1.5 | 1.8 | 2.7 | 3.0 |
| Methane/Coal Ratio | — | 4.1 | 2.9 | 4.7 | 5.3 |
| % Carbon Converted to Product | | | | | |
| $C_2H_4$ | 0 | 10.0 | 8.3 | 7.1 | 4.3 |
| BTX[1] | 0 | 2.9 | 3.4 | 6.5 | 3.6 |

[1]Predominately benzene, with trace amounts of toluene and xylene

TABLE 4

Flash Methanolysis of New Mexico Sub-bituminous Coal
Effect of Reactor Temperature

| | Run No. | | | | |
|---|---|---|---|---|---|
| | 685 | 683 | 683 | 692 | 692 |
| Reactor Temp. (°C.) | 800 | 850 | 900 | 950 | 1000 |
| Reactor Pressure (psi) | 50 | 50 | 50 | 50 | 50 |
| Coal Feed Rate (lb/hr) | 1.01 | 0.99 | 0.99 | 0.90 | 0.90 |
| Methane Feed Rate (lb/hr) | 4.1 | 4.05 | 4.05 | 4.15 | 4.15 |
| Coal Particle Residence Time (sec.) | 1.5 | 1.5 | 1.5 | 1.5 | 1.5 |
| Methane/Coal Ratio | 4.1 | 4.1 | 4.1 | 4.6 | 4.6 |
| % Carbon Converted to Product | | | | | |
| $C_2H_4$ | 6.1 | 10.2 | 10.0 | 12.6 | 12.7 |
| BTX | 0.6 | 2.1 | 2.9 | 4.2 | 8.8 |

TABLE 5

Flash Pyrolysis of New Mexico Sub-bituminous Coal With Methane

| | Run No. | | | | |
|---|---|---|---|---|---|
| | 683 | 683 | 684 | 692 | 692 |
| Reactor Temp. (°C.) | 900 | 850 | 1000 | 950 | 1000 |
| Reactor Pressure (psi) | 50 | 50 | 50 | 50 | 50 |
| Coal Feed Rate (lb/hr) | 0.99 | 0.99 | 1.0 | 0.9 | 0.9 |
| Gas Feed Rate (lb/hr) | 4.05 | 4.05 | 4.05 | 4.15 | 4.15 |
| Coal Particle Res. Time (sec.) | 1.5 | 1.5 | 1.5 | 1.5 | 1.5 |
| % Carbon Converted to Product | | | | | |
| $C_2H_4$ | 10.0 | 10.2 | 12.0 | 12.6 | 12.7 |
| $C_2H_6$ | 0 | 0 | 0.1 | 1.1 | 1.2 |
| Total Gas H.C. | 10.0 | 10.2 | 12.1 | 13.7 | 13.9 |
| BTX | 2.9 | 2.1 | 9.0 | 4.2 | 8.8 |
| Total H.C. | 12.9 | 12.3 | 21.1 | 17.9 | 22.7 |
| CO | 6.8 | 5.7 | 8.0 | 4.2 | 5.4 |
| $CO_2$ | 1.7 | 1.8 | 1.7 | 1.3 | 1.2 |
| TOTAL | 21.4 | 19.8 | 30.8 | 23.4 | 29.3 |

TABLE 6

Flash Pyrolysis of New Mexico Sub-bituminous Coal with Nitrogen

| | Run No. | | | | | | | | | |
|---|---|---|---|---|---|---|---|---|---|---|
| | 691 | 691 | 691 | 686 | 674 | 674 | 674 | 673 | 673 | 673 |
| Reactor Temperature (°C.) | 700 | 800 | 900 | 900 | 800 | 850 | 900 | 900 | 950 | 1000 |
| Reactor Pressure (psi) | 50 | 50 | 50 | 50 | 50 | 50 | 50 | 50 | 50 | 50 |
| Coal Feed Rate (lb/hr) | 1.05 | 1.05 | 1.05 | 1.34 | 1.51 | 1.51 | 1.51 | 1.29 | 1.29 | 1.29 |
| Gas Feed Rate (lb/hr) | 7.27 | 7.27 | 7.27 | 7.13 | 7.09 | 7.09 | 7.09 | 7.13 | 7.13 | 7.13 |
| Coal Part. Res. Time (sec) | 1.7 | 1.6 | 1.5 | 1.5 | 1.6 | 1.6 | 1.5 | 1.5 | 1.5 | 1.4 |
| % Carbon Conv to Product | | | | | | | | | | |
| $CH_4$ | 1.0 | 2.2 | 2.9 | 2.8 | 1.7 | 2.2 | 2.5 | 2.3 | 2.6 | 3.0 |
| $C_2H_4$ | 0 | 3.4 | 4.2 | 6.0 | 4.4 | ND | ND | 5.9 | 4.7 | 3.2 |
| Total Gas H.C. | 1.0 | 5.6 | 7.1 | 8.8 | 6.1 | | | 8.2 | 7.3 | 6.2 |
| BTX | 0 | 0.3 | 1.0 | 1.6 | 0.5 | 1.2 | 1.6 | 1.3 | 1.9 | 2.0 |
| Total H.C. | 1.0 | 5.9 | 8.1 | 10.4 | 6.6 | | | 9.5 | 9.2 | 8.2 |
| CO | ND | ND | ND | ND | ND | ND | ND | ND | ND | ND |
| $CO_2$ | 0.6 | 1.0 | 1.2 | 1.8 | 1.3 | 1.8 | 2.0 | 1.7 | 2.1 | 1.9 |

TABLE 7

Flash Pyrolysis of New Mexico Sub-bituminous Coal with Carbon Monoxide

| | Run. No. | | | | | | | | |
|---|---|---|---|---|---|---|---|---|---|
| | 677 | 677 | 677 | 681 | 681 | 681 | 682 | 682 | 682 |
| Reactor Temperature (°C.) | 900 | 850 | 800 | 900 | 850 | 800 | 1000 | 950 | 900 |
| Reactor Pressure (psi) | 50 | 50 | 50 | 50 | 50 | 50 | 50 | 50 | 50 |
| Coal Feed Rate (lb/hr) | 1.28 | 1.28 | 1.28 | 1.04 | 1.04 | 1.04 | 1.18 | 1.18 | 1.18 |
| Gas Feed Rate (lb/hr) | 7.17 | 7.17 | 7.17 | 7.17 | 7.17 | 7.17 | 7.09 | 7.09 | 7.09 |
| Coal Part. Res. Time (sec) | 1.5 | 1.6 | 1.6 | 1.5 | 1.6 | 1.6 | 1.4 | 1.5 | 1.5 |
| % Carbon Conv to Product | | | | | | | | | |
| $CH_4$ | ND | ND | ND | 6.1 | 4.9 | 4.1 | 5.3 | 5.3 | 4.7 |
| $C_2H_4$ | 6.4 | 5.5 | 4.7 | 6.5 | 6.0 | 5.1 | 2.6 | 4.9 | 6.2 |
| Total Gas H.C. | | | | 12.6 | 10.9 | 9.2 | 7.9 | 10.2 | 10.9 |
| BTX | 1.5 | 1.1 | 0.6 | ND | ND | ND | 1.8 | 1.8 | 1.3 |
| Total H.C. | | | | | | | 9.7 | 12.0 | 12.2 |
| CO | ND | ND | ND | ND | ND | ND | ND | ND | ND |
| $CO_2$ | 5.4 | 7.6 | 5.2 | 6.7 | 7.9 | 5.4 | 9.0 | 8.3 | 6.8 |

TABLE 8

Flash Pyrolysis of New Mexico Sub-bituminous Coal with Helium

| | Run No. | | | | | | | | |
|---|---|---|---|---|---|---|---|---|---|
| | 690 | 690 | 690 | 676 | 676 | 676 | 675 | 675 | 675 |
| Reactor Temperature (°C.) | 600 | 700 | 800 | 800 | 850 | 900 | 900 | 950 | 1000 |
| Reactor Pressure (psi) | 50 | 50 | 50 | 50 | 50 | 50 | 50 | 50 | 50 |
| Coal Feed Rate (lb/hr) | 0.97 | 0.97 | 0.97 | 0.98 | 0.98 | 0.98 | 1.17 | 1.17 | 1.17 |
| Gas Feed Rate (lb/hr) | 1.02 | 1.02 | 1.02 | 1.02 | 1.02 | 1.02 | 1.01 | 1.01 | 1.01 |
| Coal Part. Res. Time (sec) | 1.9 | 1.8 | 1.6 | 1.6 | 1.6 | 1.5 | 1.5 | 1.5 | 1.4 |
| % Carbon Conv to Product | | | | | | | | | |
| $CH_4$ | 0 | 2.2 | 2.5 | 2.7 | 3.6 | 4.2 | 5.1 | 4.9 | 5.0 |
| $C_2H_4$ | 0 | 2.4 | 3.7 | 4.5 | 5.4 | 5.7 | 6.1 | 4.5 | 2.3 |
| Total Gas H.C. | 0 | 4.6 | 6.2 | 7.2 | 9.0 | 9.9 | 11.2 | 9.4 | 7.3 |
| BTX | 0 | 0 | 0.3 | 0.5 | 0.9 | 1.2 | 1.7 | 1.9 | 1.8 |
| Total H.C. | 0 | 4.6 | 6.5 | 7.7 | 9.9 | 11.1 | 12.9 | 11.3 | 9.1 |
| CO | 0.5 | 1.7 | 2.8 | 2.2 | 3.0 | 3.8 | 4.5 | 4.7 | 5.9 |
| $CO_2$ | 0.5 | 0.9 | 0.9 | 1.2 | 1.4 | 1.4 | 2.0 | 2.0 | 1.8 |
| Total $CO_x$ | 1.0 | 2.6 | 3.7 | 3.4 | 4.4 | 5.2 | 6.5 | 6.7 | 7.7 |
| Total | 1.0 | 7.2 | 10.2 | 11.1 | 14.3 | 16.3 | 19.4 | 18.0 | 16.8 |

The above description and examples are provided for clarity; other embodiments of the subject invention will be apparent to those skilled in the art. Thus, limitations on the subject invention are to be found only in the claims set forth below.

We claim:

1. A process for the production of ethylene from coal in commercially significant yields greater than 10% (% carbon converted to product) comprising the steps of:
    (a) reacting coal particulates entrained in a flow of gas consisting essentially of methane with said methane gas at a temperature in the approximate range of 850° C. to 1000° C. and at a partial pressure of approximately 50 psi for a period of time of approximately 1.5 seconds; and
    (b) recovering ethylene gas produced in said reaction from the product stream comprising in addition to said ethylene, said methane and other reaction products.

2. A process as described in claim 1, wherein a portion of said other reaction products comprising tars, hydrogen sulfide, benzene, and light oils, are recovered from said methane.

3. A process as described in claim 2, wherein after said recovery a first portion of said methane is recycled for further reaction with said coal particulates.

4. A process as described in claim 2, wherein after said recovery a second portion of said methane is further processed for the removal of residual gases comprising carbon monoxide, carbon dioxide and hydrogen, said second portion then being mixed with said first portion prior to recycling, whereby the percentage of said residual gases in said recycled methane is below 20%.

5. A process as described in claim 1, wherein said reaction is carried out in a tubular reactor.

6. A process as described in claim 1, wherein said coal is a sub-bituminous coal.

* * * * *